United States Patent
Iimura (10) Patent No.: US 6,501,893 B1
(45) Date of Patent: Dec. 31, 2002

(54) PHOTOCATALYTIC OPTICAL FIBERS AND APPARATUS USING THE OPTICAL FIBERS

(76) Inventor: Keiji Iimura, 10-8, Akatsuka 3-chome, Itabashi-ku, Tokyo 175 (JP)

(*) Notice: Subject to any disclaimer, the term of this patent is extended or adjusted under 35 U.S.C. 154(b) by 67 days.

(21) Appl. No.: 09/644,418

(22) Filed: Aug. 21, 2000

Related U.S. Application Data (63) Continuation-in-part of application No. 09/146,915, filed on Sep. 2, 1998, now Pat. No. 6,108,476.

(51) Int. Cl.⁷ .................................................. G02B 6/02
(52) U.S. Cl. .......................... 385/128; 385/12; 385/123; 385/147; 422/186.3
(58) Field of Search ................................ 385/12, 123, 128, 385/147; 422/186.3, 186

(56) References Cited

U.S. PATENT DOCUMENTS 6,108,476 A * 8/2000 Iimura ......................... 385/128

* cited by examiner

*Primary Examiner*—Phan T. H. Palmer

(57) ABSTRACT

The present invention discloses a novel photocatalytic optical fiber and a novel method for activating the photocatalytic optical fiber. The photocatalytic optical fiber comprises at least an optical fiber having a core and a light input end, a photocatalytic layer including photocatalyst disposed partially or entirely on the core, wherein light is introduced from the light input end into the core and the light reflects repeatedly inside of the core, wherein said light leaks gradually from the core to the photocatalytic layer, and wherein the photocatalytic layer is activated by irradiation of the light.

31 Claims, 4 Drawing Sheets

PHOTOCATALYTIC OPTICAL FIBERS AND APPARATUS USING THE OPTICAL FIBERS

CROSS-REFERENCE TO RELATED APPLICATIONS

This is a continuation-in-part (CIP) application of U.S. patent application Ser. No. 09/146,915 filed on Sep. 2, 1998, entitled "OPTICAL FIBER WITH PHOTOCATALYST AND METHOD FOR ACTIVATING THE SAME", now U.S. Pat. No. 6,108,476 issued on Aug. 22, 2000.

BACKGROUND OF THE INVENTION

1. Field of the Invention

The invention relates to novel photocatalytic optical fiber/fibers, which include photocatalyst material.

The invention relates to a novel photocatalyst apparatus using the photocatalytic optical fibers, which include photocatalyst material.

2. Description of Related Art

It is well known that a photocatalyst (i.e. a photocatalytic material) is made of a photo-activating semiconductor typically Titanium Dioxide ($TiO_2$), it is activated by irradiation of light including relatively short wavelength such as ultraviolet (UV) light and it oxidizes and/or reduces pollutants (i.e. contaminants) so as to decomposes (i.e. dissolves or resolves) the pollutants by a photo-catalyzing reaction or effect.

The photocatalyst is capable of applying to various fields by utilizing the photo-catalyzing reaction of the photocatalyst.

That is, these fields are, for example, a cleaning to delete dirty component from a surface of articles, a dirt protection to prevent from attaching or sticking a dirty component, an infection, a deleting of offensive odor (or bad smell), a purification of gas (e.g. air) or liquid (e.g. water), a processing of exhausting gas, or a processing of waste liquid, a generation of Hydrogen and/or Oxygen from water, a speeding up of chemical reaction and a dissolving of pollutants or contaminants to cause social pollution.

All the applications as mentioned above utilize the photocatalyst reaction or photocatalyst function by strong oxidation and/or reduction power to show when the photocatalyst is activated by light.

For example, as for the purification of the air or water when the photocatalyst is irradiated by the light rays having comparatively short wavelength (e.g. ultraviolet rays), Oxygen ($O_2$) existing in the air or dissolving in the water is activated by the photo-catalyzing reaction so that Ozone ($O_3$) and/or activated Oxygen (O) generate. The Ozone or the activated Oxygen decomposes contaminants or microorganism including in the air or water, such as mold (i.e. fungi), bacteria or organic chlorine compound by an oxidization reaction. Therefore, the air or water is sterilized (i.e. disinfected, removed from microorganisms,) purified (i.e. sanitized), deodorized or discolored.

Furthermore, when the photocatalyst is irradiated by the light rays with short wavelength, it accelerates to decompose i.e. resolve the water $H_2O$ to activated oxygen (O) and/or hydrogen ($H_2$).

Moreover, the photocatalyst as a circumstance cleaning material contributes to decomposition of pollutants, which give a bad influence to a social circumstance. The pollutants are for example a volatile organic solvent, a chemical agent for agriculture such as grass eliminating agent (i.e. insecticide), an organic phosphate and a deleterious inorganic chemical compound such as cyanide and a kind of chrome.

In case that multiple photocatalyst elements (or particles) are used directly for reaction of oxidation and/or reduction with any substance, it is so difficult that the photocatalyst elements (or particles) are separated and collected, and a device to utilize the photocatalyst elements (or particles) becomes complicated and large.

While, in the case that multiple photocatalyst elements (or particles) are used as a form of photocatalyst supported substrate in which a layer including the photocatalyst elements (or particles) is fixed and supported on the substrate, the recycling of the photocatalyst elements (or particles) can be easily carried out, because the separation and collection of the photocatalyst elements (or particles) are not needed.

As for the latter case using the photocatalyst supported substrate, it is disclosed, in the publication of unexamined patent application of Japan No. 05155726 published on Jun. 22, 1993, (Japanese Patent No. 2883761 issued on Apr. 19, 1999), that a Titanium Dioxide layer (i.e. film) is formed on a substrate made of a heat resistance material such as metal, ceramic or glass in such a manner that Titania sol. is first coated on a surface of the substrate and then the Titania sol. is fired (i.e. baked). Thereby, the surface of the substrate is prevented from growth (i.e. proliferation) of bacteria.

In the related art, light rays emitting from a light source are partially used for activation of photocatalyst and the pollutants to be cleaned are irradiated indirectly by the light rays, because the pollutants exist between the light source and the photocatalyst material on the photocatalyst device. Especially, when the pollutants are made of light-absorbing or light-blocking materials, the photocatalyst material receives minimal amount of the light.

Therefore, the related art has such disadvantage that an effective use is not made for the light rays emitting from the light source. That is, a plurality of light sources and/or a light source/sources with high brightness are required to accelerate a photocatalytic reaction.

SUMMARY OF THE INVENTION

The present invention utilizes a photocatalytic (photocatalyst) optical fiber having photocatalyst material as a basic technological element that is disclosed in my U.S. patent application Ser. No. 09/146,915, now U.S. Pat. No. 6,108,476 filed on Sep. 25, 1998, further, the same basic technological element is disclosed in my Japanese Patent application No. H08/80434 filed Feb. 27, 1996 laid on 1997 in a publication of Laying-open (Unexamined) Patent Application No. 09225295A and these U.S. and J.P. applications are hereby incorporated herein by reference.

The photocatalytic optical fiber is composed of a core and a sheath being disposed partially or entirely on the core, in which the sheath includes the photocatalyst material being preferably formed as elements (or particles).

That is, a fiber like material is formed as an optical fiber by carrying the photocatalyst material corresponding to a sheath (i.e. a clad) of the optical fiber on the surface of a light-transmissible body corresponding to the core. Therefore, a light irradiation is efficiently carried out and a photo-catalyzing reaction is accelerated by irradiating directly the photocatalyst material with light output from the inside of the light-transmissible body in the photocatalytic optical fiber.

A first aspect of the present invention includes a plurality of photocatalytic optical fibers and a substrate member, in which each of the photocatalytic optical fibers are composed of a core and a photocatalytic sheath (i.e. clad, cladding, jacket, cover or coat) including photocatalyst material and the photocatalytic optical fibers are supported on the substrate member (i.e. base, support, supporter or foundation). The photocatalytic sheath is disposed partially or entirely on the core. Each photocatalytic optical fiber has a length of core, a first end and a second end.

When light is introduced (or input) from the first end and/or the second end into the core made of transparent material (i.e. light-transmissible material), the light reflects repeatedly inside of the core by means of "total internal reflection" and said light leaks gradually from the core to the photocatalytic sheath And the photocatalytic sheath is activated by irradiation of the light so that the photocatalytic sheath can be photocatalized.

A second aspect of the present invention includes a plurality of photocatalytic optical fibers and a substrate member made of transparent material, in which each of the photocatalytic optical fibers are composed of a core and a photocatalytic sheath (i.e. a photocatalytic clad) including photocatalyst material and the photocatalytic optical fibers are supported on the substrate member.

In the second aspect of the present invention, the light capable of activating the photocatalytic optical fibers may be introduced from at least one portion of the transparent substrate member to an interior of the transparent substrate member. The light is transmitted inside of the interior and output (i.e. leaked) from the interior. The leaked light is input to the cores from the first ends or the second ends (light input ends) of the photocatalytic optical fibers. The light is transmitted inside of a length of the core and also leaked gradually from the core to the photocatalytic sheath. Because the photocatalytic sheath includes the photocatalyst material, the photocatalytic sheath can be photocatalized by irradiation of the light.

A third aspect of the present invention includes a plurality of photocatalytic optical fibers and a substrate member, in which each of the photocatalytic optical fibers are composed of a core and a photocatalytic sheath including photocatalyst material and the photocatalytic optical fibers are supported on the substrate member, in which the photocatalytic optical fibers are implanted on the substrate member.

In the third aspect of the present invention, the photocatalytic optical fibers may be implanted on an adhesive member (i.e. adhesive layer or film), which is disposed partially or entirely on the substrate member. The photocatalytic optical fibers may be disposed on the substrate member by a flocking method. As the flocking method, an electrostatic flocking method is preferably utilized, in which a high voltage is applied between the photocatalytic optical fibers and the substrate member in order to flock the photocatalytic optical fibers. The adhesive member is desirably composed of light-curable resin material capable of curing by irradiation of light to fix the photocatalytic optical fibers on the adhesive material.

BRIEF DESCRIPTION OF THE DRAWINGS

Complete understandings of the present invention may be obtained from the following explanations, in connection with the accompanying drawings, in which.

DESCRIPTION OF THE PREFERRED EMBODIMENTS

The present invention will now be described in detail with reference to the accompanying drawings.

In the drawings, a relative dimension or size of each part or portion is shown as somewhat different one to clarify an explanation of the present invention and the same parts or portions have the same reference marks or numerals.

Figure 1:
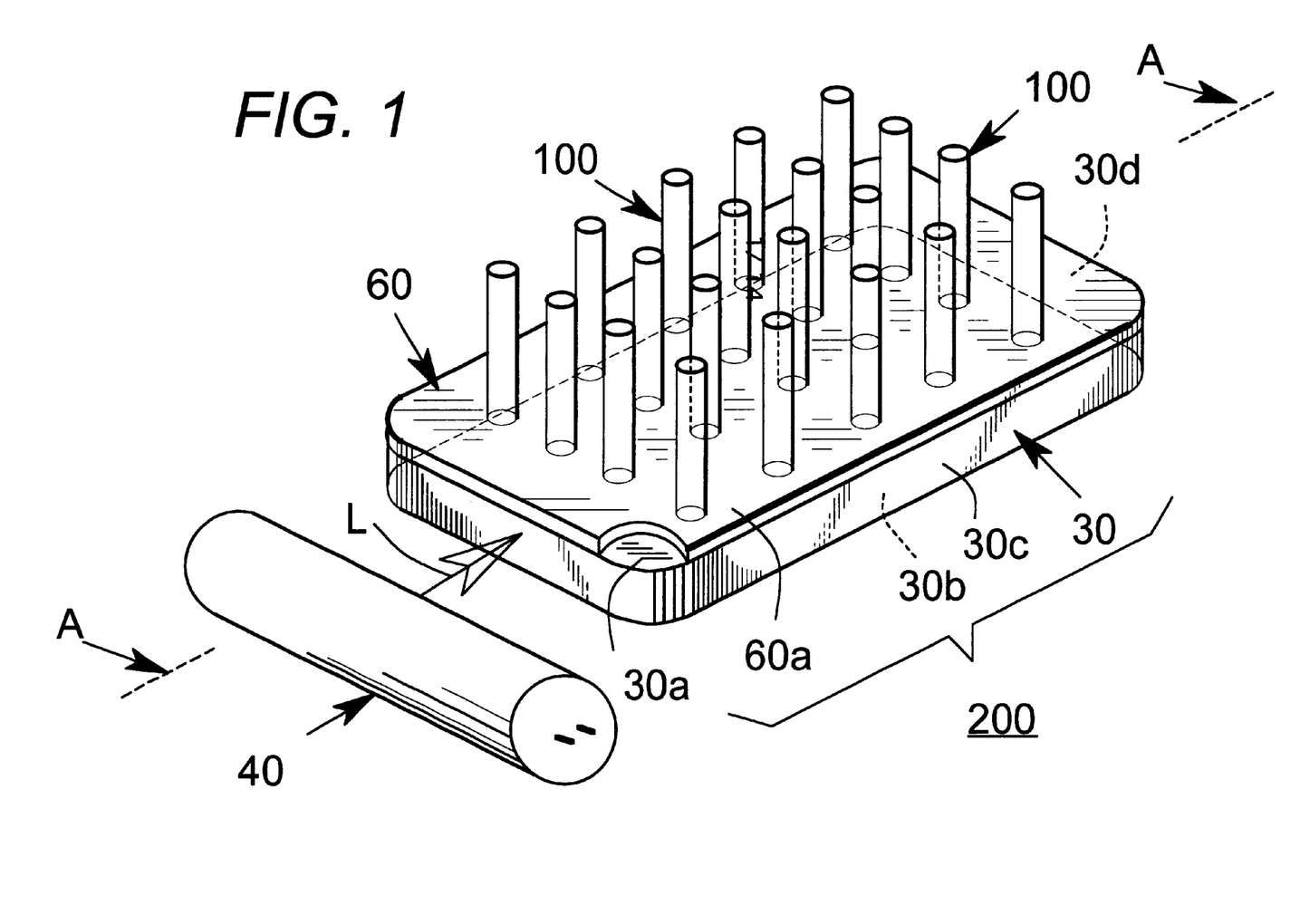
FIG. 1 is a conceptual perspective view of a first preferred embodiment of the present invention, showing a photocatalyst apparatus 200.
Figure 2:
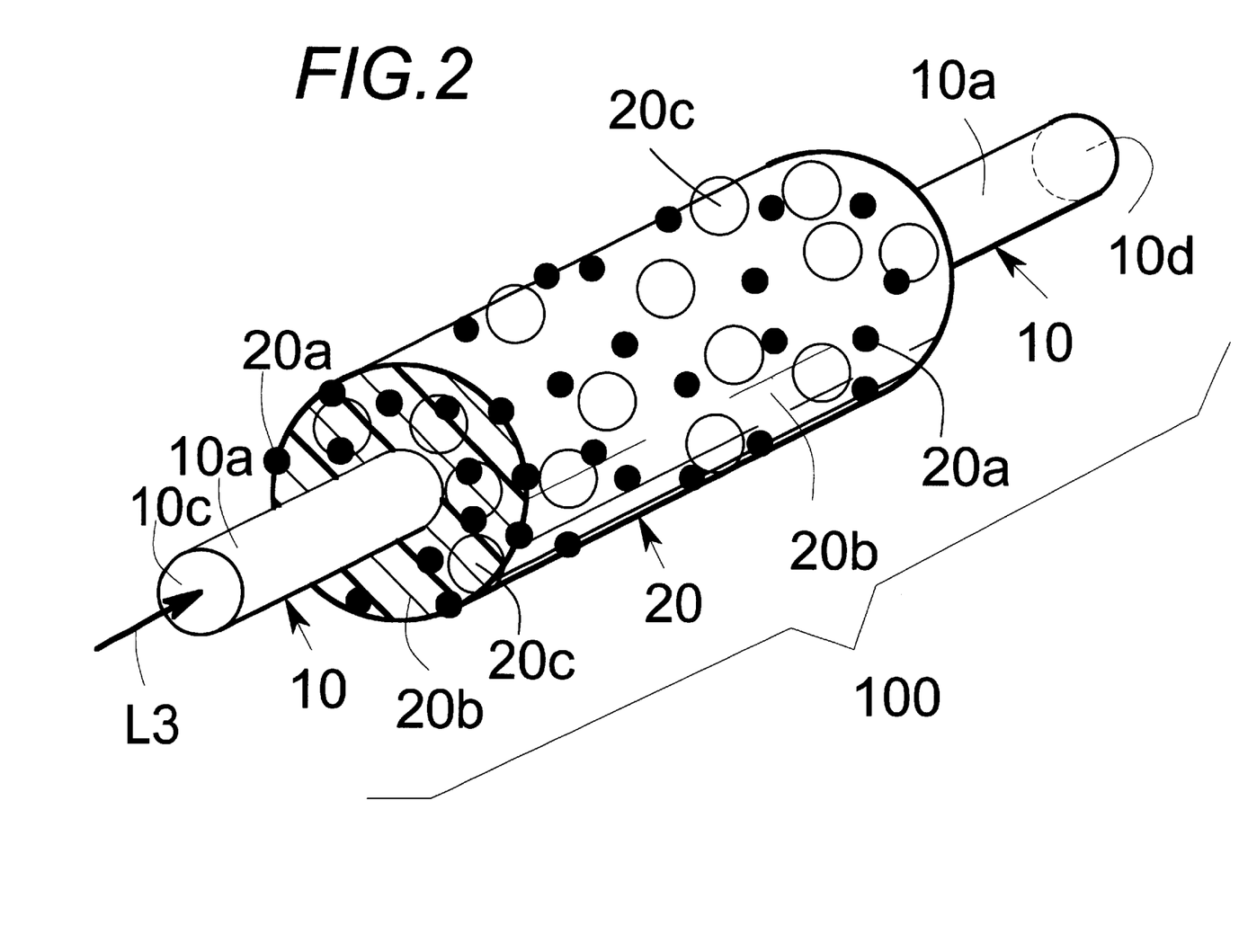
FIG. 2 is a conceptual perspective view, showing a photocatalytic optical fiber.
Figure 3:
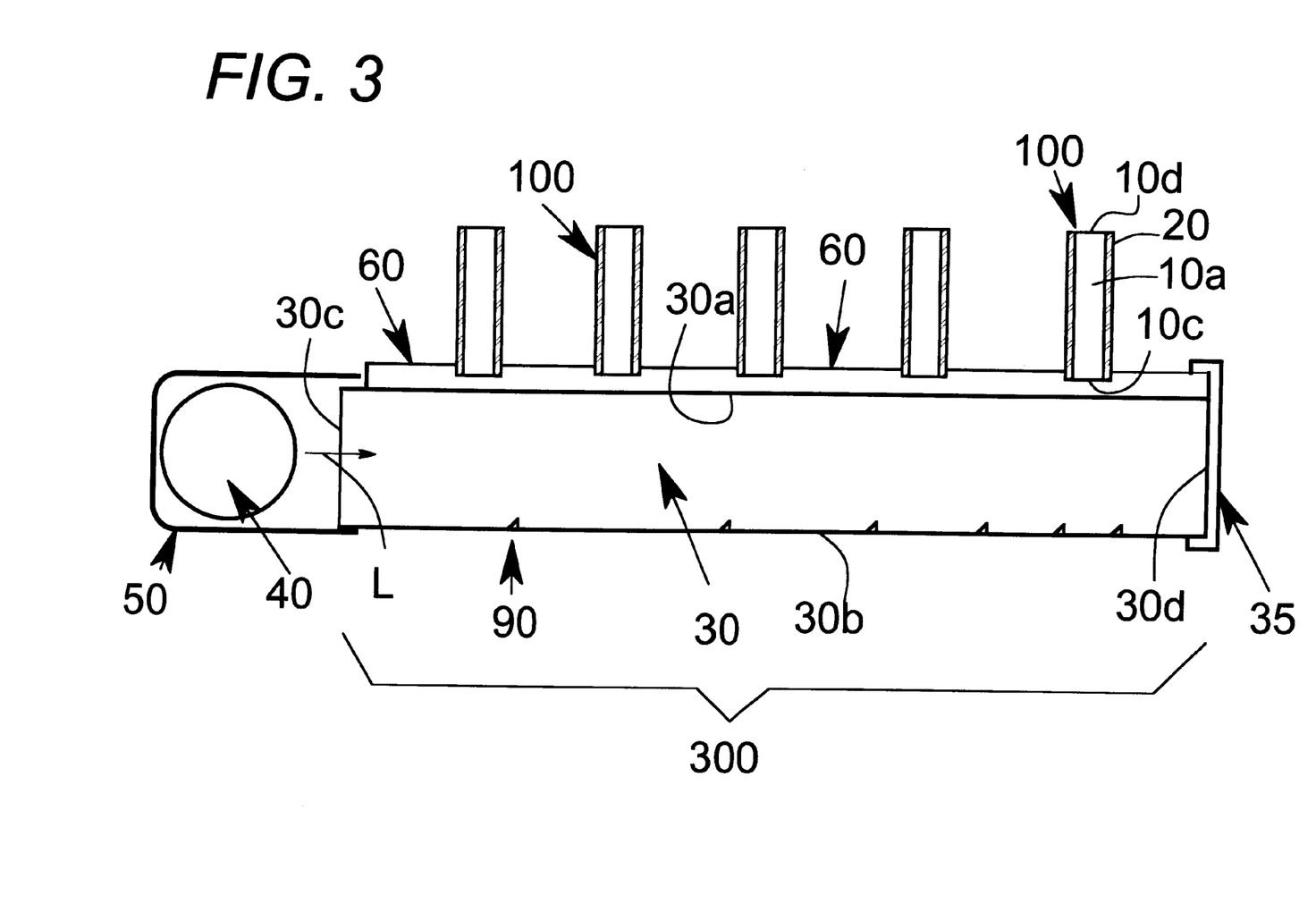
FIG. 3 is an enlarged cross sectional view along a line A—A of FIG. 1.

Reference is made to FIG. 1 to FIG. 3 showing a first preferred embodiment of the present invention.

Referring to FIG. 1, FIG. 2, FIG. 3 and FIG. 4 showing a first preferred embodiment, a photocatalyst apparatus 200 includes a plurality of photocatalytic optical fibers 100 and a substrate member 30.

Firstly, single photocatalytic optical fiber 100 will be explained in detail referring to FIG. 2.

The single photocatalytic optical fiber 100 is briefly composed of a core 10, a surface 10a of the core 10, a light-input end 10c, a light-output end 10d and a photocatalytic sheath 20. The photocatalytic sheath 20 is disposed partially or entirely on the surface 10a of the core 10. In other words: the core 10 is an optical fiber core or a core-like light transmissible body; the light-input end 10c is a proximate end or a proximate face; the light-output end 10d is a distal end or a distal face; the photocatalytic sheath 20 is a photocatalytic clad, a photocatalytic layer or a photocatalytic film.

The core 10 is made of transparent material capable of transmitting light rays such as UV (ultraviolet) light. The photocatalyst sheath 20 includes photocatalyst material and may be composed of a plurality of photocatalyst elements (or particles) 20a and a binder 20b capable of transmitting the light rays. The photocatalyst elements (or particles) 20a may be dispersed in the binder 20b. In other words, the photocatalyst elements (or particles) are photocatalyst elements, photocatalyst powders or photocatalyst pieces.

The core 10 further may be preferably made of transparent inorganic or organic material capable of transmitting light lays including the UV light. The transparent inorganic material suitable for use in the core 10 are typically made of Fused Quarts (including more than 99.9 weight % of $SiO_2$), Sapphire, Borosilicate glass (composing of $SiO_2$; 75.3, $B_2O_3$; 13.8; ZnO; 1.4, $Al_2O_3$; 4.3, NaO; 5.0 weight %). The transparent organic (i.e. polymer) material suitable for use in the core 10 are typically made of Silicone resin (Dimethyl Silicone, etc.), Acrylic resin (Polymethyl Methacrylate, etc.), Polycarbonate resin (PC) and UV transmissible Fluoric resin (Polyfluoroethylene), Polyethylene resin, Polyester resin, or epoxy resin.

The photocatalyst elements (or particles) 20a may be made of photo-activated semiconductors such as Titanium Dioxide; $TiO_2$ (photo-activation wavelength; not more than 388 nm), Tungsten Dioxide; $WO_2$ (photo-activation wavelength; not more than 388 nm), Zinc Oxide; ZnO ( photo-activation wavelength; not more than 388 nm), Zinc Sulfide; ZnS (photo-activation wavelength; not more than 344 nm) and Tin Dioxide $SnO_2$ photo-activation wavelength; not more than 326 nm).

The binder (i.e. paint) 20b capable of transmitting the UV light rays L1 may be made of transparent organic material such as Silicone resin, Acrylic resin, Polycarbonate resin and UV transmissible Fluoric resin, etc. The binder 22 is made of inorganic material capable of transmitting the UV light rays L1 such as transparent glass flit, instead.

Alternatively, the photocatalytic sheath 20 may be made from Titania sol, which is preliminarily coated on the core 10 and treated by high temperature of about 500° C., then the Titania sol changes to Titanium Dioxide.

A first transparent material used for the core 10 and a second transparent material used for the sheath 20 are so selected that a refractive index of the core 10 is higher than that of the sheath 20, similar to a conventional optical fiber excluding a photocatalyst.

However, a refractive index of the core 10 may be equal to that of sheath 20 or a refractive index of the sheath 20 may be higher to than that of the core 10, in which both cases differ from the conventional optical fiber excluding a photocatalyst.

The UV light rays L1 emitting from a UV light source are projected to the light-input end 10c of the photocatalytic optical fiber 100. The UV light rays L1 are transmitted to another terminal i.e. a distal end 10d of the photocatalytic optical fiber 100 according to an optical principle of "internal total reflection". The UV light rays L1 reflect repeatedly along a length of the core 10 and simultaneously the UV light rays L1 are leaked out from the core 10 to the photocatalytic sheath 20 to activate the photocatalyst elements (or particles) 21, which are dispersed in the photocatalytic sheath 20.

The photocatalytic sheath 20 may preferably include absorption material (i.e. an adsorbent) capable of absorbing a pollutant (i.e. contaminant) such as gaseous material in addition to the photocatalyst material. The adsorbent may be composed of simple substance or composite such as active carbon, zeolite, porous ceramics or silica gel. The absorbent may be formed as elements (or particles). A mixture of the photocatalyst elements (or particles) 20a and the absorbent elements (or particles) 20c may be disposed (or dispersed) in/on the photocatalytic sheath 20 (i.e. the binder layer). Alternatively, the photocatalyst elements (or particles) 20a may be preferably carried on each absorbent particle (or element) having larger size than each photocatalyst particle. A plurality of the absorbent elements (or particles) 20c, each absorbent particle 20c carrying the photocatalyst elements (or particles) 20a may be disposed (or dispersed) in/on the sheath 20 (binder layer).

In the sheath 20 including a composite of the photocatalyst and absorbent as mentioned above, the absorbent is always absorbing the pollutant until a capacity of absorbing is saturated and the photocatalyst is activated by irradiation of the light rays L3. The photocatalyst oxidizes and/or reduces the pollutant being contacted directly with the photocatalyst at the time of light-irradiation. At the same time, the pollutant absorbs the pollutant being storing in the absorbent.

Therefore, it should be noted that since the absorbent is used with the photocatalyst, a large amount of the pollutant can be treated to be oxidized and/or reduced by photocatalizing of the photocatalyst.

As is shown in FIG. 1 and FIG. 3, the photocatalyst apparatus 200 is composed of a substrate member 30 and a plurality of photocatalytic optical fibers 100, in which the plurality of photocatalytic optical fibers 100 is disposed on the substrate member 30. The photocatalytic optical fibers may be implanted partially or entirely on the substrate member 30. The substrate member 30 may be made of substantially transparent material capable of transmitting light including relatively short wavelength light rays such as ultraviolet (UV) light rays. For example, the substrate member 30 may be formed as a transparent panel 30 (i.e. plate) having a substantially rectangular-shaped body. The rectangular-shaped body 30 has a first surface 30a (a front surface), a second surface 30b (a rear surface) opposed to the first surface 30a, a first side face (i.e. side or facet) 30c, a second side face 30d opposed to the first side face 30c.

The transparent substrate member 30 may be made of organic transparent material (typically, acrylic resin or polycarbonate resin) or inorganic transparent material (typically, fused-quarts or glass), which is the same as transparent material used for the core 10 and/or the sheath 20 of the optical fiber 100 as described above.

As is shown in FIG. 3, for more detail, an adhesive member 60 (i.e. an adhesive layer or film) may be disposed on the front surface 30a of the substrate member 30. The adhesive layer 60 is preferably made of substantially transparent resin (i.e. polymer) material such as Silicone resin, Acrylic resin, Polycarbonate resin and Fluoric resin, Polyethylene resin, Polyester resin or epoxy resin, which is equivalent to the transparent material of the sheath 20. When the adhesive member (adhesive layer) 60 is made of curable resin i.e thermo-setting or light-setting plastic, an implantation of photocatalytic optical fibers to the substrate member 30 may be processed by an electrostatic flocking method.

The electrostatic flocking is widely used typically in a textile industry and conventionally applied by two main methods, a direct current (DC) electrostatic flocking and an alternating current (AC) electrostatic flocking. An adhesive layer is formed on a substrate by coating an adhesive material. Multiple flock fibers are contained in a hopper having the mesh screen at a bottom of the hopper and a vibrator. A high voltage, DC or AC in the range of 30,000 volts to 120,000 volts is applied between an electrically conductive mesh screen (a charging electrode) or a separate charging electrode) and the adhesive layer. An electric charge is given to the individual fibers from the charging electrode. The flock fibers are transferred onto the adhesive layer on the substrate, so that the flock fibers are oriented vertically and embedded or implanted on/in the adhesive layer.

As is shown in FIG. 3 again, liquid resin is mixed with curing agent (i.e hardener) in advance. The liquid resin in an uncured state is preliminarily coated on the front surface 30a of the panel 30 by a conventional coating method. The conventional coating method may be a printing, spraying, immersing or transferring method. A high voltage of DC or AC is applied between the substrate member 30 (or the adhesive layer 60) and the plurality of photocatalytic optical fibers so that the photocatalytic optical fibers are transferred (i.e. removed or propelled) toward the adhesive layer 60 by electrostatic field attraction. Accordingly, the plurality of photocatalytic optical fibers is implanted temporarily on or in the adhesive layer 60 under the uncured state. Then, the uncured resin is cured by applying a cured condition of the uncured resin, in which curing is carried out by heating in a high temperature more than a room temperature or by irradiation of light rays such as UV light, until the adhesive layer 60 is hardened. Thereby, the photocatalytic optical fibers are fixed permanently on the adhesive layer 60.

Instead of the curable resin (i.e. thermo-setting resin), thermo-plastic resin (i.e. hot-melt resin) may be used for the adhesive member 60. The thermo-plastic resin is preliminarily coated on the front surface 30a of the panel 30. The thermo-plastic resin coating (adhesive layer) 60 is heated in a sufficient temperature more than a room temperature during application of the high voltage or after an implantation is accomplished so that the adhesive layer 60 is melt. Then, the coating 60 is cooled less than the room temperature until the coating is hardened to fix the photocatalytic optical fibers on the adhesive layer 60.

A third transparent material used for the transparent panel 30 and a fourth transparent material used for the adhesive layer 60 in cured or hardened state are so selected that a refractive index of the transparent panel 30 is higher than that of the adhesive layer 60. However, the transparent panel 30 may be equal to or lower than the adhesive layer 60 in the refractive index.

The transparent panel 30 may be provided with a light-diffusing (i.e. light-scattering) means 90 disposed on the rear surface 30b as shown in FIG. 3 (and/or the front surface 30a). The light-diffusing means 90 may be composed of a plurality of micro-projections, micro-grooves or micro-prisms positioned on the rear surface 30b (and/or the front surface 30a). The light-diffusing means 90 are acting as a light-diffuser in which light diffuses or reflects toward the adhesive layer 60 so as to irradiate the optical fibers 100. Further, the light-diffusing means 90 have preferably a graduation pattern, in which a pitch of the micro-projections, micro-grooves or micro-prisms is gradually changed from the first side face 30c to the second side face 30d.

When only the single light source 40 is positioned adjacent to the first side face 30c, a pitch for positioning the micro-projections, micro-grooves or micro-prisms on the rear surface 30b may be increased gradually from the first side face 30c to the second side face 30d so as to produce a uniform surface brightness for irradiating or lighting uniformly most of the optical fibers 100 as is shown in FIG. 3.

When the photocatalytic optical fibers 100 of the photocatalyst apparatus 300 are photo-catalized by light irradiation, the photocatalyst material included in the photocatalytic optical fibers are activated in order to oxidize and/or reduce a substance/substances being contacted, closed to, or stuck on the photocatalytic optical fibers so that the substance/substances are subjected to be cleaned-up or processed to react for clarification. At the same time, the photocatalyst apparatus 300 itself is cleaned-up so as to have a self-cleaning characteristic, thereby maintenance work for clarifying the photocatalyst apparatus 300 is reduced.

Referring again to FIG. 2 and FIG. 3, the light rays L2 input to the adhesive layer 60 further transmit toward the photocatalytic optical fibers and outside. The light rays L3 directing to the photocatalytic optical fibers are received at the light-input end (or the first end) 10c of the photocatalytic optical fibers and transmit inside of a length of the core 10 of the photocatalytic optical fibers toward the second end. Some volume of the light rays L3 leak i.e. output to the photocatalytic sheath 20 including the photocatalytic elements 20a. Therefore, the photocatalytic sheath 20 is photocatalized by irradiated of the light rays L3. Further, some volume of the light rays L4 directing to outside via the transparent adhesive layer 60 transmit toward the photocatalytic optical fibers for irradiating the photocatalytic optical fibers from an exposed surface of the photocatalytic optical fibers. Therefore, the photocatalytic optical fibers can receive the light rays L3 from an interior of the photocatalytic optical fibers and, at the same time, the light rays L4 from an exterior of the photocatalytic optical fibers. Furthermore the adhesive layer 60 may further include photocatalytic material, for example, the photocatalytic material may be formed as elements (or particles) and the elements (or particles) may be formed on a surface of the adhesive layer 60 or may be dispersed in the adhesive layer 60 instead.

It should be noted that an optimum use of the light rays from the light source is accomplished efficiently without loss of light by utilizing the transparent substrate member (i.e. light-guidable member) applying an edge-lighting effect and the plurality of photocatalytic optical fibers disposed on/in the transparent substrate member and that most light rays from the light source can contribute irradiation of the photocatalytic optical fibers in the first aspect of the present invention.

Figure 4:
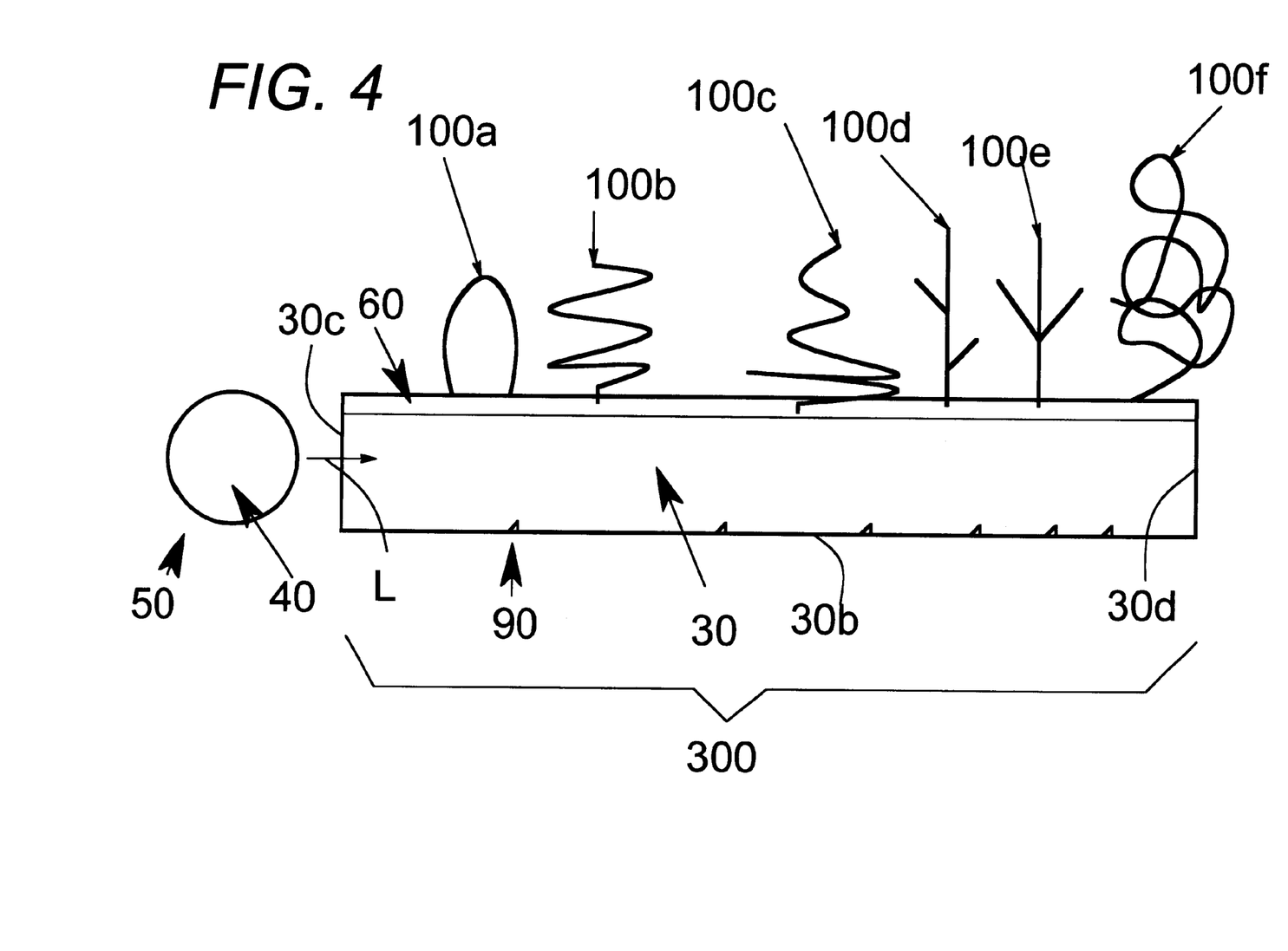
FIG. 4 is a side elevational view showing various modifications of the present invention.

Referring to FIG. 4, various modification of the present invention is illustrated, in which various modifications are made in the afore-mentioned first embodiment. The photocatalytic optical fiber 100 including the photocatalyst (or the composite of the photocatalyst and the absorbent) may be modified to any patterns or shapes.

The numeral 100a denotes a photocatalytic optical fiber having a U-shape, in which the optical fiber 100a has a length of core being bent to form the U-shape, a first end and a second end. The first end and the second end are implanted on the surface of the transparent panel 30 so as to receive or accept the light L output via the panel 30. In this case, a total quantity of the optical fibers 100a can be reduced. The numeral 100b and 100c denotes each photocatalytic optical fiber having a coil-shape, respectively, in which the optical fiber 100b or 100c has a length of core being bent to form the coil-shape, a first end or a second end. The first end or the second end is implanted on a surface of the transparent panel 30 so as to receive light output via the panel 30. In this case, the light may be leaked from bent portions of the optical fiber 100b and 100c to a photocatalytic sheath on the core by a bending loss of the optical fiber. The optical fiber 100b or 100c is composed of a plurality of substantially circular portions, in which the optical fiber 100b has substantially uniform diameter, while the optical fiber 100c has substantially different diameter. The numeral 100f denotes a photocatalytic optical fiber having a random-shape, in which the optical fiber 100f has a length of core being extend in a random fashion to form the random-shape, a first end and a second end. The first end or the second end is implanted on the surface. The numeral 100d or 100e denotes a photocatalytic optical fiber having a trunk optical fiber and a plurality of branched optical fibers, both optical fiber having the photocatalyst and the absorbent, respectively. At least dual branched optical fibers in the photocatalytic optical fiber 100e are elongated upwardly from the same portion of the trunk optical fiber, while at least dual branched optical fibers in the photocatalytic optical fiber 100d are elongated upwardly from different portions of the trunk optical fiber.

Although illustrative embodiments of the present invention have been described referring to the accompanying drawings, it is to be understood that the present invention is not limited to those embodiments and that various changes, modifications, or equivalents may be made in the present invention by those skilled in the art without departing from the spirit or the scope of the present invention and the appended claims.

What is claimed is:

1. Photocatalytic optical fibers comprising:
   a plurality of photocatalytic optical fibers, each of said photocatalytic optical fibers being composed of a core, a sheath (or clad) to cover partially or entirely said core and a photocatalyst material included in said sheath; and light-leaking means for outputting light from an interior of said core to said photocatalyst material.

2. The photocatalytic optical fibers according to claim 1:
wherein said core has a plurality of light-leaking portions that acts as said light-leaking means.

3. The photocatalytic optical fibers according to claim 1:
wherein said core has a plurality of light-leaking portions that acts as said light-leaking means;
wherein said light-leaking portions are selected from the group consisting of micro-grooves, micro-projections and micro-prisms, which are disposed in/on a surface of said core.

4. The photocatalytic optical fibers according to claim 1:
wherein said core has a plurality of light-leaking portions that acts as said light-leaking means;
wherein said light-leaking portions form a graduation pattern in which a pitch for positioning said light-leaking portions are gradually changed from a first end of the core toward a second end of the core, or vice versa.

5. The photocatalytic optical fibers according to claim 1:
wherein said core has a plurality of light-leaking portions that acts as said light-leaking means; and
wherein said light-leaking portions form a graduation pattern in which a pitch of said light-leaking portions are gradually increased from a first end of the core toward a second end of the core or vice versa so as to produce a substantially uniform surface brightness.

6. The photocatalytic optical fibers according to claim 1:
wherein said sheath has a refractive index higher than or equal to said core and thereby said sheath acts as said light-leaking means.

7. Photocatalytic optical fibers comprising:
a plurality of photocatalytic optical fibers, each of said photocatalytic optical fibers being composed of a core, a first sheath (or clad) to cover partially or entirely said core and a second sheath to cover partially or entirely said first sheath; and
a photocatalyst material being included in said second sheath.

8. The photocatalytic optical fibers according to claim 7:
wherein said first sheath has a refractive index higher than or equal to said core.

9. The photocatalytic optical fibers according to claim 7:
wherein said first sheath has a refractive index lower than said core.

10. Photocatalytic optical fibers comprising:
a plurality of photocatalytic optical fibers, each of said photocatalytic optical fibers being composed of a core and a sheath (or clad) to cover partially or entirely said core; and
a photocatalyst material and an absorbent material being included in said sheath.

11. The photocatalytic optical fibers according to claim 10:
wherein said photocatalyst material and is composed of a plurality of photocatalyst elements and said absorbent material is composed of a plurality of absorbent elements; and
wherein a mixture of said photocatalyst elements and said absorbent elements are disposed in/on said sheath.

12. The photocatalytic optical fibers according to claim 10:
wherein said photocatalyst material is composed of a plurality of photocatalyst elements and said absorbent material is composed of a plurality of absorbent elements;
wherein each of said absorbent elements includes a plurality of said photocatalyst elements to form a composite element; and
wherein a plurality of said composite elements is disposed in/on said sheath.

13. The photocatalytic optical fibers according to claim 10:
wherein said sheath is composed of a first sheath to cover partially or entirely said core and a second sheath to cover partially or entirely said first sheath;
wherein said first sheath includes said photocatalyst material and said second sheath includes said absorbent material.

14. The photocatalytic optical fibers according to claim 10:
wherein said sheath is composed of a first sheath to cover partially or entirely said core and a second sheath to cover partially or entirely said first sheath;
wherein said first sheath is made of substantially transparent material having a refractive index lower than a refractive index of said core; and
wherein said second sheath includes said photocatalyst material and said absorbent material.

15. The photocatalytic optical fibers according to claim 10:
wherein said sheath is composed of a first sheath to cover partially or entirely said core and a second sheath to cover partially or entirely said first sheath;
wherein said first sheath is made of substantially transparent material having a refractive index higher than or equal to a refractive index of said core; and
wherein said second sheath includes said photocatalyst material and said absorbent material.

16. The photocatalytic optical fibers according to claim 10:
wherein said photocatalytic optical fiber is formed as a linear shape.

17. The photocatalytic optical fibers according to claim 10:
wherein said photocatalytic optical fiber is formed as a non-linear shape selected from the group consisting of a coil-shape, a random shape, a U-shape and a branched shape.

18. A photocatalytic apparatus comprising:
a plurality of photocatalytic optical fibers, each of said photocatalytic optical fibers being composed of a core and a photocatalytic sheath (or clad) including photocatalyst material; and
a substrate member to support said photocatalytic optical fibers, being made of substantially transparent material.

19. The photocatalytic apparatus according to claim 18, further comprising:
an additional sheath excluding said photocatalyst material and being interposed between said core and said photocatalytic sheath.

20. The photocatalytic apparatus according to claim 18, further comprising:
an additional sheath excluding said photocatalyst material and being interposed between said core and said photocatalytic sheath; and
wherein said additional sheath has a refractive index higher than or equal to said core.

21. The photocatalytic apparatus according to claim 18, further comprising:

an additional sheath excluding said photocatalyst material and being interposed between said core and said photocatalytic sheath; and wherein said additional sheath has a refractive index lower than said core.

22. The photocatalytic apparatus according to claim 18, further comprising:

an absorbent material disposed in/on said photocatalyst sheath.

23. The photocatalytic apparatus according to claim 18:

wherein said photocatalytic sheath is disposed partially or entirely on said core.

24. The photocatalytic apparatus according to claim 18:

said photocatalytic sheath being composed of a plurality of photocatalyst elements and a binder to dispose said photocatalyst elements on said core.

25. The photocatalytic apparatus according to claim 18:

said photocatalytic sheath being composed of a plurality of photocatalyst elements and a binder to dispose said photocatalyst elements on said core; and wherein said binder has a refractive index higher than or equal to said core.

26. The photocatalytic apparatus according to claim 18:

said photocatalytic sheath being composed of a plurality of photocatalyst elements and a binder to dispose said photocatalyst elements on said core; and wherein said binder has a refractive index lower than said core.

27. The photocatalytic apparatus according to claim 18:

said each of said photocatalytic optical fibers further having a first end and a second end; and wherein said first end and/or said second end are disposed on said substrate member.

28. The photocatalytic apparatus according to claim 18:

an adhesive member being made of substantially transparent material and being disposed partially or entirely on said substrate member.

29. The photocatalytic apparatus according to claim 18, further comprising:

a plurality of non-photocatalytic optical fibers excluding photocatalyst material; and wherein said photocatalytic optical fibers and said photocatalytic are disposed partially or entirely on said substrate member.

30. The photocatalytic apparatus according to claim 18, further comprising:

an adhesive member being disposed partially or entirely on said substrate member;

photocatalytic material being disposed on said adhesive member; and wherein said photocatalytic optical fibers are implanted on said adhesive member.

31. The photocatalytic apparatus according to claim 18, further comprising:

an adhesive member being disposed partially or entirely on said substrate member;

photocatalytic material being composed of a plurality of photocatalytic elements disposed on said adhesive member; and wherein said photocatalytic optical fibers are implanted on said adhesive member.

* * * * *